United States Patent
Hamacher

(10) Patent No.: US 6,919,475 B2
(45) Date of Patent: Jul. 19, 2005

(54) PROTECTED TYROSINE DERIVATIVES, METHOD FOR THE PRODUCTION THEREOF AND USE OF THE SAME FOR PRODUCING O-(2-[$^{18}$F]-FLUOROETHYL)-L-TYROSINE

(75) Inventor: Kurt Hamacher, Aachen (DE)

(73) Assignee: Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 10/480,004

(22) PCT Filed: May 29, 2002

(86) PCT No.: PCT/EP02/05887

§ 371 (c)(1),
(2), (4) Date: May 24, 2004

(87) PCT Pub. No.: WO02/102765

PCT Pub. Date: Dec. 27, 2002

(65) Prior Publication Data

US 2004/0192954 A1 Sep. 30, 2004

(30) Foreign Application Priority Data

Jun. 5, 2001 (DE) .......................... 101 27 126

(51) Int. Cl.$^7$ ............................................ C07C 229/00
(52) U.S. Cl. ....................................................... 560/155
(58) Field of Search ......................................... 560/155

(56) References Cited

U.S. PATENT DOCUMENTS 5,885,548 A * 3/1999 Maier et al. ............... 424/1.65

OTHER PUBLICATIONS

Webster et al, Journal of Nuclear Medicine, (1999) 40(1) pp205–212.*

* cited by examiner

Primary Examiner—Cecilia J. Tsang
Assistant Examiner—Hector M. Reyes
(74) Attorney, Agent, or Firm—Schweitzer Cornman Gross & Bondell LLP

(57) ABSTRACT

The compound O-(2-[$^{18}$F]fluoroethyl)-L-tyrosine has proven to be particularly suitable for positron emission tomography and has already been tested in clinical practice. Until now, the compound has been prepared according to a relatively laborious method (Wester H. J. et al., J. Nucl. Med. 1999; 40: 205–212).

The invention relates to L-tyrosine derivatives of the formula (1)

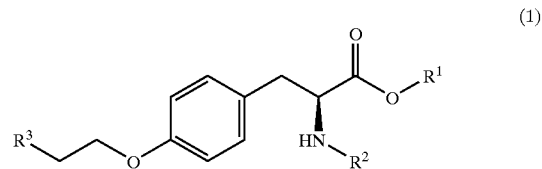

(1)

whereby $R^1$ represents a suitable protective group for the carboxy group, $R^2$ a suitable protective group for the amino group and $R^3$ a suitable leaving group, $R_1$ represents a methylthiomethyl group, a tetrahydrofuranyl group, a diphenylmethyl group, a para-methoxybenzyl group, a piperonyl group or a tert-butyl group, $R^2$ an alkyl- or an arylalkyl group and $R^3$ a p-tosyloxy, methanesulfonyloxy, trifluoromethanesulfonyloxy or bromine.

The invention also relates to a method for preparing O-(2-[$^{18}$F]-fluoroethyl)-L-tyrosine from the initial compounds of formula (1) and method for the preparation of these initial compounds.

8 Claims, No Drawings

PROTECTED TYROSINE DERIVATIVES, METHOD FOR THE PRODUCTION THEREOF AND USE OF THE SAME FOR PRODUCING O-(2-[$^{18}$F]-FLUOROETHYL)-L-TYROSINE

The invention relates to a method for the preparation of O-(2-[$^{18}$F]fluoroethyl)-L-tyrosine, novel compounds as initial material for the preparation of O-(2-[$^{18}$F]fluoroethyl)-L-tyrosine and a method for the preparation of this initial material.

The diagnosis of brain tumors is performed lately more and more through the positron emission tomography (PET)-method.

In the beginning the investigations related to the PET-method were concentrated on the investigation of glucose metabolism, using the compound $^{18}$F-fluorodeoxyglucose (FDG) as a diagnostic. With this labelled compound the results were not satisfactory in all cases, in particular since glucose is accumulating in the whole brain and for this reason no sufficient contrast can be observed between normal tissue and tumor tissue and henceforth a satisfactory distinction of tumor tissue from healthy brain tissue is not possible.

More satisfactory were the experiences with labelled amino acids. Promising results were achieved initially with the amino acid $^{11}$C-methionine. These results proved that reliable investigations can be performed for the determination of brain tumors and the course of a therapy. At first it was assumed that an increased protein synthesis in the tumor tissue is the cause of the increased amino acid concentration, but nowadays it is assumed that the reason is a change of the amino acid transport. Such a change of the amino acid transport can be investigated not only with the normal physiologic amino acids, but also with amino acid derivatives which themselves cannot be used for protein synthesis.

The investigations with $^{11}$C-methionine displayed however the practical disadvantage that the half-life of $^{11}$C of 20 minutes is very short and the PET investigations with $^{11}$C-methionine (and of course with other $^{11}$C-labelled compounds) can only be performed in or in the immediate vicinity of an institute where the short-living positron emitter $^{11}$C can be prepared.

To overcome the disadvantage of the short half-life of $^{11}$C, further investigations were performed with 18F-labelled amino acids. The half-life of $^{18}$F is with 110 minutes much more favorable compared with $^{11}$C. Such a half-life allows a preparation in a central facility with subsequent transport to other institutions and doctor's surgeries. In the meantime, experiences with 4-[$^{18}$F]-fluoro-L-proline, O-(2-[$^{18}$F]fluoroethyl)-L-tyrosine 1-amino-3-[$^{18}$F]fluorocyclobutane carboxylic acid and 3-[$^{18}$F]fluoro-α-methyl-L-tyrosine are available. The compound O-(2-[$^{18}$F]fluoroethyl)-L-tyrosine was found out to be highly suitable and is already tested in the clinical practice (Weber W. A. et al.; Eur. J. Nucl. Med. 2000; 27: 542–549).

The preparation of O-(2-[$^{18}$F]fluoroethyl)-L-tyrosine used to be performed with a relatively laborious method (Wester H. J. et al.; J. Nucl. Med. 1999; 40: 205–212).

This method comprised the preparation in a first step of [$^{18}$F]fluoroethyl tosylate, and in a second step unprotected L-tyrosine (as the di-potassium salt) is reacted herewith.

A disadvantage of this preparation is the need to purify by chromatography the $^{18}$F-fluorinating reagent before further reaction.

It was an object of the present invention to provide a less laborious preparation of O-(2-[$^{18}$F]fluoroethyl)-L-tyrosine.

It was a further object of the present invention to provide initial material for the preparation of O-(2-[$^{18}$F]fluoroethyl)-L-tyrosine.

It was yet a further object of the present invention to provide a way of preparing the initial material.

The invention relates initially to novel initial material for the preparation of O-(2-[$^{18}$F]-fluoroethyl-L-tyrosine ([$^{18}$F]FET) according to the formula (1):

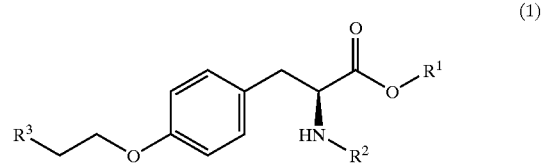

whereby $R^1$ is a suitable protective group for the carboxy group and $R^2$ is a suitable protective group for the amino group.

The group $R^3$ is suitable leaving group for the fluorination of the initial material of the formula (1) to the corresponding fluorinated compound.

Suitable groups $R^1$ are ones which protect the carboxy group under the particular reaction circumstances. As will be described later in more detail in connection with the description of the method of the invention, it is a preferred embodiment to perform the method in a dipolar aprotic solvent. The group $R^1$ shall have the function, in this preferred embodiment of the method, not to be split off under the conditions of the nucleophilic $^{18}$F-fluorination. It is wanted, that the group $R^1$ can be split off easily under acid conditions in a last step of the method together with the group $R^2$.

Such suitable groups $R^1$ are for instance such rests, which can also be split off under strongly acid conditions in an organic, non-aqueous solvent.

Preferred groups $R^1$ according to the invention are the methylthiomethyl group, the tetrahydrofuranyl group, the diphenylmethyl group, the para-methoxybenzyl group, the piperonyl group and the tert-butyl group.

Most preferred for the group $R^1$ is the tert-butyl group.

Suitable groups $R^2$ are such ones which protect the amino group of the amino acid under the particular reaction circumstances. As will be described in more detail later in connection with the method of the invention it is a preferred embodiment to perform the method in a dipolar aprotic solvent. The group $R^2$ shall in this preferred embodiment have the function of providing the protective effect specifically under the conditions of the nucleophilic $^{18}$F-fluorination and of preventing a racemisation of the L-amino acid. It is desired that the group can be split of easily in a last step of the method.

Such groups are for instance alkyl- or arylalkyl groups.

Preferred groups $R^2$ according to the invention are carbamates such as tert-butylcarbamate, p-methoxybenzylcarbamate, diphenylmethylcarbamate and the triphenylmethyl group. Most preferred is the triphenylmethyl group.

The group $R^3$ represents a suitable leaving group. This group is substituted in the actual fluorination method through fluorine-18.

Preferred groups $R^3$ in the scope of the invention are p-tosyloxy, methanesulfonyloxy, trifluoromethanesulfonyloxy and bromine.

A particularly preferred group $R^3$ is the p-tosyloxy group.

It has turned out that the compounds of the formula (1) should be present in crystalline form, which makes their handling and dosing substantially more easy.

The compounds of the formula (1) are in particular suited as initial material for the preparation of O-(2-[$^{18}$F]fluoroethyl)-L-tyrosine.

The method of the invention for the preparation of O-(2-[$^{18}$F]fluoroethyl)-L-tyrosine provides $^{18}$F-fluorinating an initial compound of the formula (1) in a first step and splitting off the protective groups R$^1$ and R$^2$ in a second step, thereby obtaining the desired final compound O-(2-[$^{18}$F]fluoroethyl)-L-tyrosine.

For the fluorination a compound of the formula (1) is reacted in the presence of a phase transfer system, for instance of the formula R$_4$N$^{+18}$F, whereby R represents an alkyl group with 3 to 6 carbon atoms, preferably n-butyl. $^{18}$F is prepared through a method which is known in the art, by the conversion of water enriched with $^{18}$O through a (p,n)-nuclear reaction in a cyclotron into [$^{18}$F]fluoride.

The fluorination is performed with the aid of a phase transfer catalyst. As such phase transfer catalysts in principle catalysts such [K⊂2.2.2]$_2$CO$_3$ and (TBA$^+$HCO$_3^*$) come into consideration.

It has been shown that a yield of approximately 10% can be achieved when the fluorination step is performed with [K⊂2.2.2]$_2$CO$_3$ as the catalyst.

Furthermore, it has been shown, that this result can be improved by performing the fluorination step with (TBA$^+$HCO$_3^-$) as the catalyst. When the particularly preferred initial compound N-trityl-O-(2-tosyloxyethyl)-L-tyrosine tert-butyl ester is used as the initial compound for the preparation of O-(2-[$^{18}$F]fluoroethyl)-L-tyrosine, a radiochemical yield of more than 80% is achieved with (TBA$^+$HCO$_3^*$) as the catalyst. This represents a surprisingly good result.

As the solvent for the nucleophilic $^{18}$F-fluorination the usual organic solvents come into consideration. It has been shown that the reaction proceeds particularly well with an aprotic solvent such as for instance acetonitrile, N,N-dimethyl acetamide, N,N-dimethyl formamide, dimethyl sulfoxide and hexamethylphosphoric triamide, whereby acetonitrile is particularly suited due to its physico-chemical properties.

The first step is usually performed at a temperature of approximately 85° C.

A duration of 5 minutes is usually sufficient for the performance.

After termination of the first step, as mentioned before, after approximately 5 minutes the deprotection is performed. It is not necessary to perform a prior purification and the circumstance that the second step of the deprotection proceeds in the same container as the first step, and hence the method relates to a one-pot reaction, is an attractive aspect of the present invention.

The deprotection itself is initiated by the addition of a strong acid, this should be an acid which can also be used in a non-aqueous system such as for instance dichloromethane. The deprotection proceeds particularly well with trifluoroacetic acid.

After the deprotection the compound O-(2-[$^{18}$F]fluoroethyl)-L-tyrosine is available in unpurified form.

The last purification step of the final compound O-(2-[$^{18}$F]fluoroethyl)-L-tyrosine is performed with usual tools and methods. The separation of the labelled amino acid can be performed very favorably through solid-phase extraction from the organic phase. The use of silica gel and aluminum oxide is recommendable in this connection. When this extraction is performed with silica gel and aluminum oxide, acid which is usually adsorbed at the solid phase is largely removed through a suitable elution step. It is not particularly important what solvent is taken for the elution, but for the selection of the solvent it plays a role what acid was taken and what solid phase combination was used. In general it has turned out, that a mixture of n-pentane and diethylether is very suitable for this elution step in particular when trifluoroacetic acid is used.

After the elution the remaining solvent rest which is adhering to the solid phase can be evaporated and removed with an inert gas such as nitrogen or argon and the labelled amino acid can be extracted with a suitable buffer solution. Usually such a buffer solution is used which allows an immediate HPL-chromatography.

It is the major advantage of the method of the invention, that the labelled amino acid can be prepared with relative ease in a one-pot reaction. The method allows the preparation while avoiding racemisation. The use of [$^{18}$F]fluoride guarantees a no-carrier added final product, which is required for an administration to patients. It is the advantage of the method of the invention, that a preparation of a labelled amino acid with a molar activity of more than 18,5 GBq/μmol is possible without undue efforts.

The preparation of the initial compounds of the formula (1) can be performed with methods which are known in the art. It is possible in the preparation to use the amino acid L-tyrosine as the basis and to select the further reactants depending on the wanted final product.

When an initial compound of the formula (1) which comprises as the group R$^1$ a tert-butyl group needs to be prepared, it is convenient to start with the compound L-tyrosine tert-butyl ester, since this compound is available commercially. Otherwise L-tyrosine is combined in a first step with a reagent which is capable of reacting with the carboxy group, thereby forming a compound of the formula (2):

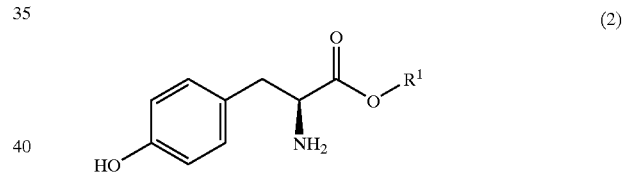

(2)

Hereby R$^1$ has the same meaning as described in connection with the description of the initial compounds according to the invention. Suitable reagents for the performance of the reaction are in particular alcohols such as for instance tert-butanol or the olefin isobutene.

In a second step the compound of the formula (2) reacts with a compound R$^2$X whereby a compound of the formula (3)

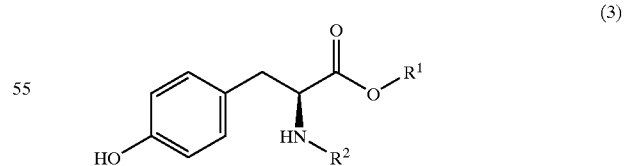

(3)

is formed. The group R$^2$ has hereby the same meaning as described in connection with the description of the initial compounds according to the invention. X represents a halogen, preferably chlorine.

In a next step the compound of the formula (3) is converted into a compound of the formula (1), whereby in this last step a R$^3$—C$_2$H$_4$— group is introduced at the hydroxyl group of the aromatic ring. Suitable reagents for this last step are 1,2-bifunctional ethylene derivatives, such as for instance ethylene glycol di (p-toluolsulfonate) and 2-bromoethanol.

It is a preferred embodiment of the compounds of the formula (1), that the group $R^3$ is a tosyloxy group, for this preferred embodiment the last step is performed with ethylene glycol di (p-toluolsulfonate).

The invention is now described in more detail on the basis of the following examples:

EXAMPLE 1

Preparation of O-(2-tosyloxyethyl)-N-(triphenylmethyl)-L-tyrosine tert-butyl ester First Phase N-triphenylmethyl-L-tyrosine tert-butyl ester L-Tyrosine tert-butyl ester* was reacted at room temperature in DMF, in the presence of triethylamine, with an equimolar amount of triphenylmethylchloride. Through mixing of the DMF phase with the 4-fold amount of ice the raw product is precipitated and recrystallized from ethanol.

Yield: 70% Fp. 171° C.

(*Commercially Available)

Second Phase O-(2-Tosyloxyethyl)-N-(triphenylmethyl)-L-tyrosine tert-butyl ester:

Equimolar amounts of N-triphenylmethyl-L-tyrosine tert-butyl ester and ethylene glycol di-(p-toluolsulfonate) were dissolved in acetone. The educt mixture was stirred intensely for two days at room temperature. After filtration and evaporation of the solution containing the raw product, the purification of the product was performed through column chromatography on silica gel with an elution agent (?Laufmittel?) consisting of low boiling petroleum ether and ethyl acetate.

Yield: 60% Fp. 54 . . . 64° C.

EXAMPLE 2

Preparation of O-(2-[$^{18}$F]fluoroethyl-L-tyrosine)

The $^{18}$F-containing water was evaporated in the presence of 40 μmol tetra-n-butylammonium-hydrogen carbonate to dryness. Thereafter a solution of 25 mg (37 μmol) N-trityl-O-(2-tosyloxyethyl)-L-tyrosine tert-butyl ester in 0.5 ml acetonitrile was added and the solution heated to boiling for 5 minutes. Under reduced pressure the solvent was evaporated, at a temperature of approximately 20° C. 1 ml of a mixture of trifluoracetic acid/triethylsilane/dichloromethane (1/0,4/2) (v/v/v) was added and stirred for 10 minutes. After dilution with 9 ml dichloromethane the solution was led through a silica gel- and subsequently an aluminum oxide cartridge (1 g each). The cartridges were washed with 10 ml of a solvent mixture consisting of n-pentane/diethylether (1/1). The remaining solvent was evaporated through a stream of inert gas, the [$^{18}$F]FET raw product was eluted with the help of a 35 mmol trisodium phosphate solution and purified through reversed phase High Pressure Liquid Chromatography. The [$^{18}$F]FET product fraction was led through a cation exchanger (LiCnrolut SCX, H$^+$-form, 1 g), thereafter washed with sterile water and the $^{18}$F-labelled amino acid eluted with a sodium phosphate buffer of physiologic concentration and the eluate sterile filtrated.

What is claimed is:

1. L-Tyrosine derivative of the formula (1)

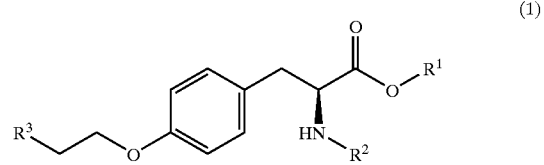

(1)

whereby $R^1$ is a protective group far the carboxy group selected from the group consisting of a methylthiomethyl group, a tetrahydrofuranyl group, a diphenylmethyl group, a para-methoxybenzyl group, a piperonyl group or a tert-butyl group, $R^2$ is a protective group for the amino group represented by an arylalkyl group and $R^3$ represents a suitable leaving group represented by p-toluenesulfonyloxy, methanesulfonyloxy, trifluoromethanesulfonyloxy or bromine.

2. The tyrosine derivate according to claim 1, whereby $R^1$ represents a tert-butyl group, $R^2$ a triphenylmethyl group and $R^3$ a toluenesulfonyloxy-group.

3. A method for the preparation of O-(2-[$^{18}$F]fluoroethyl)-L-tyrosine whereby an initial compound of the formula (2)

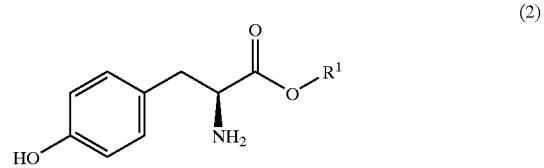

(2)

is converted with $R^2X$ to a compound of the formula (3)

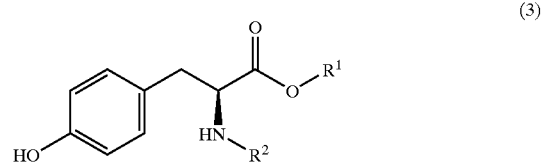

(3)

and the compound of the formula (3) is converted in a second step into a compound of the formula (1) through the reaction of the hydroxyl group with a 1,2-bifunctional ethylene derivative.

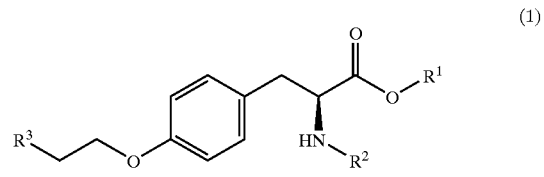

(1)

and the compound of the formula (1) reacts in a third step with a tetraalkylammonium[18F]fluoride of the formula

or a cryptate of the formula

[K⊂2.2.2]¹⁸F in the presence of a phase transfer catalyst,
in an aprotic solvent,
to the compound of the formula (5)

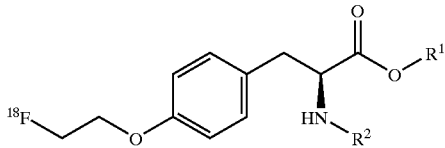

(5)

and the groups R¹ and R² are split off in a separate step in an acidic system and the resulting product O-(2-[18F]fluoroethyl-L-tyrosine) is thereafter purified, whereby R¹, R² and R³ have the same meaning as in claim 1, X represents halogen and R represents an alkyl group with 3 to 6 carbon atoms.

4. The method according to claim 3, whereby R is an n-butyl group.

5. The method according to claim 3, whereby the phase transfer catalyst is tetrabutylammonium hydrogen carbonate.

6. The method according to any of claims 3 to 5, whereby the aprotic solvent is selected from the group consisting of acetonitrile, N,N-dimethyl acetamide, N,N-dimethyl formamide, dimethyl sulfoxide and hexamethylphosphoric triamide.

7. The method according to any of claims 3 to 5, whereby the acidic system in the last step of the method comprises trifluoroacetic acid in dichloromethane.

8. The method according to claim 6, whereby the acidic system in the last step of the method comprises trifluoroacetic acid in dichloromethane.

* * * * *